(12) United States Patent
Strong et al.

(10) Patent No.: US 6,677,444 B1
(45) Date of Patent: Jan. 13, 2004

(54) MELANOMA ANTIGENS AND METHODS OF USE

(75) Inventors: Theresa Strong, Birmingham, AL (US); Robert M. Conry, Birmingham, AL (US); Albert F. LoBuglio, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 623 days.

(21) Appl. No.: 09/691,538

(22) Filed: Oct. 18, 2000

Related U.S. Application Data

(60) Provisional application No. 60/160,042, filed on Oct. 18, 1999.

(51) Int. Cl.[7] .............................................. C07H 21/04
(52) U.S. Cl. .................. 536/23.5; 435/325; 435/320.1; 536/24.31
(58) Field of Search ............................. 536/23.5, 24.31; 435/320.1, 325, 69.1, 252.33, 410, 348; 514/44; 424/277.1

(56) References Cited

PUBLICATIONS

Lue RA, et al. Proc Natl Acad Sci USA 1994; 91: 9818–22.*
Sohail, et al, Current Opinions in Molecular Therapy 2000; 2: 264–271.*
Pierce, et al, Nucleic Acids Research 1998; 26: 5093–5101.*
Lesoon–Wood, et al, Cancer Letters 1999; 147: 163–173.*
Yamshchikov, et al, Clinical Cancer Research 2001; 7: 909s–916s.*
Bodey, et al, Anticancer Research 2000; 20: 2665–2676.*
Cox, et al, Science 1994; 264: 716–719.*
Ezzell, Journal of NIH Research 1995; 7: 46–49.*
Spitler, Cancer Biotherapy 1995; 10: 1–3.*
Boon, Advances in Cancer Research, 1992; 58: 177–210.*
Arceci, Journal of Molecular Medicine 1998; 76: 80–93.*
Lee, et al, Journal of Immunology 1999; 163: 6292–6300.*
Zaks, et al, Cancer Research 1998; 58: 4902–4908.*
Gura, Science 1997; 278: 1041–1042.*
James, Antiviral Chemistry & Chemotherapy 1991; 2 (4): 191–214.*
Roush, Science 1997; 276: 1192–1193.*
Smith et al, Clin Cancer Res Dec. 2001; 7 (12): 4253–4261.*
Conry et al, Clin Cancer Res Nov. 1998; 4 (11): 2903–2912.*
Bocchia et al, Haematologica 2000; 85: 1172–1206.*
Gao, P, et al, J Immunther 2000; 23 (6): 643–653.*

* cited by examiner

Primary Examiner—Anthony C. Caputa
Assistant Examiner—Stephen L. Rawlings
(74) Attorney, Agent, or Firm—Benjamin Aaron Adler

(57) ABSTRACT

The present invention provides for isolated DNA and protein corresponding to novel melanoma tumor-associated antigens, antibodies directed towards the novel antigens of the present invention as well as methods of using the antigens for inhibiting the growth of a melanoma tumor and methods of screening compounds that inhibit the novel antigens of the present invention.

7 Claims, 10 Drawing Sheets

50/50 Mix of positive clone 3.1 + negative insert 3.1 5' end

```
atggnatntg tttgaancct attttgaaac cttgccanct cgaantaacc    50
ctcataaggg caacaaanct ggagctcgcg cgcctgcagg tcganactag   100
tggttccaaa gaattcggca cgagcctaat caaggagaag actgctattt   150
ttttttctat tccacatgta ccaaaggcga cagctgccca ttccgtcact   200
gtgaagctgc aataggaaat gaaactgttt gcacattatg caagaaggg    250
cgctgttttc gacaggtgtg caggtttcgg cacatggaga ttgataaaaa   300
acgcagtgaa attccttgtt attgggaaaa tcagccaaca ggatgtcaaa   350
aattaaactg cgctttccat cacaatagag gaccgatatg ttgatggcct   400
tttcctacct ccgagcaaaa ctgtgttgcc cactgtgcct gagtcaccag   450
aagaggaaag tgaangctan cncaantttc agttcaagct ggaacaaaat   500
tggctnntcc aatnccaaat cccttcccct taaacctggn ggaaaccgtt   550
antgaaaagt tagnaaattt tcccgaaaat tgttct    SEQ ID NO: 1  586
```

3.1 3' end

```
cgcctggaaa agggtaagta acccagggac ggagccttgg gtaaagtgtg    50
tcatccccca attggcccaa cgtaagcagt gagatgccgc tgtgtcattg   100
ccgctgtgaa cctcagtcca caggtcctac aggaccccca gccaaaaagg   150
cagctgtggc tgttgtcccg cttgtcttga ggcaaatcag tcctgtgcct   200
gaagcagaaa atcctagagc agtcttgtgc tgcctccaac ccagtccttt   250
cagattcctc accccagag gtgtctggcc ctcctcatcc caatgagcat   300
gaaaactgcc gactcagctt tgcctcaaca ggaaagcccc cactcttgtg   350
gaggatgatt ttagaaacta atatgggaga tttcaggagg caaattggaa   400
gctgagattg acctggatct gggaaaatga atgacccttt gcttgagcta   450
tcaaaatgat tatagctgaa ggtggtagtg aggacccttt aaaaaaaaaa   500
tcgccaaaaa ctggcttagt ttcattattg aactttacct gagatgatct   550
ttttagtta gaatttgccc caatcaaaga accttgaatt atccaaaaaa   600
aaaaaaaaaa aaaaa                          SEQ ID NO: 2   615
```

Fig. 2A 3.14 5' end

```
ggggtatnnt ttgaaccttc nttctccant taaccctcat aagggaacaa    50
anctggactc gcgcgcctgc aggtcgacac tagtggatcc aaagaattcg   100
gcacgagttt atcttagccg gaggacctgc tgatctaagt ggagagctca   150
gaaaaggaga tcgtattata tcggtaaaca gtgttgacct cagagctgct   200
agtcatgagc aggcagcagc tgcattgaaa aatgctggcc aggctgtcac   250
aattgttgca caatatcgac ctgaagaata cagtcgtttt gaagctaaaa   300
tacatgattt acgggagcag atgatgaata gtagtattag ttcagggtca   350
ggttttcaaa tggttcctga ggttttttgt tgttgtccgt gttgttactg   400
ttgttcttgt catcaggttt gattttggtc cttgcccttt ccttctagtt   450
ctcctttat taataggaaa ggnaggcaaa agccccatt tatgtggggg     500
ggttttcccc ttaanacagc ttttcattcc acctggttct gcacntaaaa   550
ttggccccaa aatcttcatt ggng               SEQ ID NO: 3   574
```

3.14 3' end

```
accgtgttga actaaaactt ttcgggccca tttttaaatg gggttttcag    50
ggcccgtttt caaaaggttc ctaaggtttt tgttgtgccc gggttgtaac   100
tggttgttct gtcatcaggt ttgattttgg gcccttgccc tttccttcta   150
gttctccttt tattaatagg aaggcaggca aaagcccccat ttatgtggtg  200
ttttcccctc agacagcttt catccactgc tctgcactag aattgcacaa   250
atcttcatgg tgagcaattt taagaaatgt tagtaaaagg tagaaattat   300
ttcacaaatc agtttctctg gtccttcata ttaataataa tatttggctt   350
cccattgctc tttggagttg tttattaaat atgtgttttt gacaacctcc   400
tcattagttt cttaaatgag tactggtttg taaagaatta tcaacattat   450
ccattccatt tatgaagaag aggagaacag ctaataaact gtattgaaat   500
ccaaaaaaaa aaaaaaaaaa aaaaaaaa         SEQ ID NO: 4     528
```

Fig. 2B 3.3T 5' end

```
aggnnggagc actcagctcg aaattnaccc tcactaaagg gaacaaaagc      50
tggagctcgc gcgcctgcag gtcgacacta gtggatccaa agaattcggc     100
accaggaaat ccagaaatta gtcatatgtt gaataatcca gatataatga     150
gacaaacgtt ggaacttgcc aggaatccag cantgatgca ggagatgatg     200
aggaaccagg accgancttt gancaaccta naaagcatcc caggggatn      250
tnatgcttta aggcgcatgt ncacagatat tcatgaacca atgctgagtg     300
ctgcacaaaa acaanttggg gggaaaccat ttgcttcctt gngaacaaat     350
natccnnngn ggaaggnagn cnanccttcc cgtccngaaa tttnnattcc     400
cntcccatnc cttggncccn naactcccaa atttntaaat ttcnacggcc     450
tgcacctggg ngggcantcg gttcctgcca gnggccttttt ggnanatann    500
ctgccaaatt ggcccgngag agaactnttt tttcaacaca caaaatg       547
                                              SEQ ID NO: 5
```

3.3T 3' end

```
ttttccgtga gaaacattca gttaaacaca ggggggggatc accagctaat     50
aaagggtatg ggtcccctca tacagcattt tgtttttaaa aaatggattt    100
atttttgtaa cgggtttaaa ctttaaaaac ccgctttatt tcatttgctt    150
tgggaattgg cgttaaacca accccaatta gccttttaag ggggctaaag    200
gggggtttcg gaattttttt ttcggaggga ataagggaag gagatcttgc    250
attaatggat ttttaaaacc ccccttttaaa gtggggggacc agattttgtc  300
ctgcatctgt ccagttattt gcttttttaaa catagcctat ggtagtaatt   350
tatgtagaat aaaagcatta aaagaagca aatcatttgc tctctaaaaa     400
aaaaaaaaaa aaa                               SEQ ID NO: 6  413
```

Fig. 2C 5.17 5' end

```
aggnntaggt naccctacta aagggaacaa aagctggagc tcgcgcgcct    50
gcaggtcgac actagtggat ccaaagaatt cggcacgagc cgactcggtc   100
acaaggaaaa tggattcagt ttgcatctct ccctccttta aacagcttct   150
ccgggtctca gcatggtatc aaagcttgaa agagagaaga ctcaagaagc   200
gaagaggatt cgtgagctgg agcagcgcaa gcacacggtg ctggtgacag   250
aactcaaagc caagctccat gaggagaaga tgaaggagct gcaggctgtg   300
agggagaacc ttatcaagca gcacgagcag gaaatgtcaa ggacggtgaa   350
ggtacgtgat ggaagaagat ccagaggctc aagtctgctc tctgtgctct   400
ccgcgacggc agcagtgacc aaagtaagga cagcgctacc attgaggccc   450
ggnaaggagg cccgaaacct gtttgaccca nacgccttaa gctttacngg   500
naaattgcgg acctgaaacg gccaaaagcc nggggccaa aggttttgcc    550
antttgatcc caaggccnna nntttatag tgggcntnga nggcnttatc    600
cncaaacctt taanat                                SEQ ID NO: 7    616
```

5.17 3' end

```
gtaccccga aaagggttta cccttaaggg caattgttcc ccccccct      50
aagggttcca aagttaagat tcccctgaa cggctaaggg ttttaaagcc   100
ttattcaagg tttcttactt gccagttcct accaaaccct gtaaaatctc   150
caataatgct gcatttaatg aaacatggta tatgtcaaat cagaagagaa   200
gaactataaa catatattgt gtaaagaaaa agttcagcaa tggaactagt   250
tttgcagatc aagcaaagat gtgtcttggg catggaacca aagttacaat   300
gaaatattca acccctgctg tgcaggggg tcatttaat gtaacaccac     350
accccatgga aacactagtc ctgataataa acatcatttt aaaagatcaa   400
aacaaacaaa caaaaaaaac aagggtgggt ggggagtgaa gcacgaggaa   450
tacctatgaa gagctattta caataaaatg tttcatttga aaaaaaaaa    500
aaaaaaaaa                                        SEQ ID NO: 8   510
```

Fig. 2D 5.23

```
ggacaacagc tggagctcgc gcgcctgcag gtcgacacta gtggatccaa  50
agaattcggc acgagagaaa gtaaggaaaa gttcagggta tagaaatagc 100
tattcagtga ctttgtattt ttacttgtgc tcttaagaac ctttattcat 150
gtaatgcaaa gtaatttgtg ttgaagttga acttgtgaga aaatatatag 200
tacctaatgc attctcattt ggaatatgtg atctgtagaa atggaaatat 250
ttttatttat tttactgttt ttataggagg ttcgtaaagt gaatgaaagc 300
atcaagataa tcacccattg agaaatgtg ttgatacaat acttaaaaag 350
tgccctacag agtatcagga aaaatgggt aggaacatgg atgattatga 400
agatttgat gaaaagcata gtatctatcc agtgaaaaaa gtctggtaaa 450
actgccataa acaggggact tgctaatta taagtatttt actaatgatg 500
attttaatt agacttctaa tcattgctca taaaaaaagg aattttttagt 550
gaatgtgtat ttaaaacttc ctttaatccc gtccttatca ttctttgaaa 600
tattttatct ctgtgtatac cagcaggggt attattggcg tttggggagg 650
gagaattctt cactgagcat aactgttaca ttatataaaa ctgttacatc 700
attttggaac attaatattc tcagcctgac ccagtaaatg ccctagcact 750
ttcccattgt tatgacaatc caaacatgct ccctagtgga gagttgaacc 800
actgttggat cagaacactg ccaggtctac ccccattctc tttttaggt 850
gatttattca gttcagagac accgtcgaac tcaagtacaa tggcagattc 900
ttttggaaca agcatttat ctagaagatg tagcaaaaaa tgaaactagt 950
gctactcatc agtttgttca cacctttcaa tcgccagagc cagaaaatcg 1000
atttatccaa tatttttata atcctacatt tggtatgtaa tttgatataa 1050
atttcaaact ttaatgatga aaagttttct gtagaaagaa gttatgtatt 1100
ttcaccaatg caaagttgaa ttttatttgt attatttgat ttataccatg 1150
tgatattaag tatctggtaa catttcccca aaataactgt tttacttatc 1200
atataacata taatccatca gtttccactg ttacttcaca aataataaaa 1250
attctattaa aaaacatgta tacatcaagc atattttta taatgcataa 1300
tatatacaat tatgcattgc ttaatgactg ggattactct gagaaatgta 1350
ttgttaggca atttcatcac tgcatgagca tcatagggta tgtactaaac 1400
ctagatggta tagtacaggt aggcaaatat gggtattggc ttattactcc 1450
taaggctaca aaacctatac agcatggtta ctgtacctga aagtggtagg 1500
cagttgtaca ccagggtttt tggtttttaa acttgaaaaa tatttttaaa 1550
agccgttgta attttggggg atcacccttt ttttgcaccc tctttggccg 1600
ggaggtgtat tgaccctat gtcctttaaa aatagaaatt tagtattttt 1650
cttccagctt tggtttttt ttatttgaac tatatttttgg ttaattcctc 1700
ttgatattaa cctttatagt ttttcaggaa attagttaaa atccgttgta 1750
ttttatggtc cccatttagc gtccttcatg ggtggaagtt tttatgtgac 1800
acaaggctga taaaaaggtt aaatttttaa gttatttttct caccaggctg 1850
gggttttttc ttcagtcttg aacaaacaac tgaaatttgg cttaagtaag 1900
tcctccttga tattaaccat ttattagtct taattataaa accctatact 1950
ttgtaggtta tcatttttttc tccttttttg ctaaatttat gggcaatccc 2000
```

Fig. 2E

```
ttccaagtat ttgtcaaatt tagtgtgaag aaacttaaaa gcaaggtacc 2050
aaaagtgtca tagtattaaa acttctattt accttattta tttaaaaaa 2100
attgttatat tcacttgatt tctccctttg catgtttggt tttgagtatg 2150
aagacttaat ggctataaca aatatctcag aaaactcctt taacaaaaat 2200
ccttcctaat taaatgaagg aatgatgtgt tatctgtttt cattcattca 2250
acaaatattt gggtacatta gtgctatgta ttattgggtg ctgggtagct 2300
tggtatatat cagtttaaaa agacagaaat tcctgccctt gtggagtgag 2350
aaaaacagac aataaacata taaaggcata aagattctga ataggcagtt 2400
gattatagaa attgaaattc aagggaggag tctgaattgc agatatgaat 2450
tagggtacca tcaatgtgta gggaaccatg gggtcaggat aaaatcaata 2500
aagaagtaat tgagatagag aaaagagaaa agtctgagga ccaagcctga 2550
ggcactccag aatttagaga ttaggtggat gagaagtaac tagcagaaaa 2600
gactagaaaa ggaggggcca gtgagatagg aaaattagga caatgaagtg 2650
ttttgaggaa aagagtatat aaagtacctt ttcaaatgtt gcacatagat 2700
taaggatcat atatattaag acctgaccat tggattttag agaagtgagg 2750
ggagaggata aaaagtctg actgtaattt aaaagaaata agaagaggag 2800
caattggaga cagactagaa aactctaaaa atgttttcct tataaaaggg 2850
aacagagaaa aggggtagta gctgaaagag gattgggggc atagtcaaga 2900
gaaattatca catgtaatta gtaaatgata taatagaatt tgaggccagg 2950
cgcggtggct cacacctgta atcccagcac tttgggaggc cgaggcggca 3000
gatcacaagg tcaagagatt gagaccatcc tggccaacat ggtgaaaccc 3050
cgtctctact aaaaatacaa aaattagctg ggcgtggtgg tgcgtgcctg 3100
tagtcccagc tactcgggag gctgaggcag gagaatcctt gaacaggagg 3150
cggaggttgc agtgagccga gattgtgcca tgcactccag cctacctgta 3200
gtcccagcta ctcgggaggc tgaggcagga gaatcacttg aacccaggag 3250
gtggaggttg cagtgagccg agattgcgcc actgcactcc agcctacctg 3300
tagtcccagc tacttgggag atgaggcagg agaatcgctt gaacccggga 3350
ggcagaggtt gcagtgagcc aagattgcac cactacactc cagcctgggg 3400
acagaatgag actccgtcaa aaaaaaaaa aaaaactcga gagtacttct 3450
agagcggccg cgggcccatc gattttccac ccgggtgggg taccaggtaa 3500
gtgtacccgt cg                    SEQ ID NO: 9  3512
```

Fig. 2F 5.28

```
ggacgccgct ggagctccgc gcctgcaggt cgacactagt ggatccaaag 50
aattcggcac cagcctgcag gtactgctgc tcgtgcctcc ggctccggcc 100
cctgagcgat ggtcctttcc ttctgccacg gcgggatcgg cactcaccc 150
agttgcaagt gcgagcacta tggagtagcg cagggtctcg agctgtggcc 200
gtggacttag gcaacaggaa attagaaata tcttctggaa agctggccag 250
atttgcagat ggctctgctg tagtacagtc aggtgacact gcagtaatgg 300
tcacagcggt cataaaacaa aaccttcccc ttcccagttt atgcctttgg 350
tggttgacta cagacaaaaa gctgctgcag caggtagaat cccacaaac 400
tatctgagaa gagaggttgg tacttctgat aaagaaattc taacaagtcg 450
aataatagat cgttcaatta ggaccgctct tccagctgg ctacttctat 500
gatacacagg ttctgtgtaa tctgttagca gtagatggtg taaatgagcc 550
tgatgtccta gcaattaatg gcgcttcgta gccctctcat tatcagatat 600
tccttggaat ggacctgttg gggcagtacg aataggaata attgatggag 650
aatatgttgt taacccaaca agaaaagaaa tgtcttctag tactttaaat 700
ttagtggttg ctggagcacc taaaagtcag attgtcatgt tggaagcctc 750
tgcagagaac attttacagc aggacttttg ccatgctatc aaagtgggag 800
tgaaatatac ccaacaaata attcagggca ttcagcagtt ggtaaaagaa 850
actggtgtta ccaagaggac acctcagaag ttatttaccc cttcgccaga 900
gattgtgaaa tatactcata aacttgctat ggagagactc tatgcagttt 950
ttacagatta cgagcatgac aaagtttcca gagatgaagc tgttaacaaa 1000
ataagattag atacggagga acaactaaaa gaaaaattc cagaagcccg 1050
atccatatga aataatagaa tccttcaatg ttgttgcaaa ggaagttttt 1100
agaagtattg ttttgaatga atacaaaagg tgcgatggtc gggatttgac 1150
ttcacttagg aatgtaagtt gtgaggtaga tatgtttaaa acccttcatg 1200
gatcagcatt atttcaaaga ggacaaacac aggtgctttg taccgttaca 1250
tttgattcat tagaatctgg tattaagtca gatcaagtta taacagctat 1300
aaatgggata aaagataaaa atttcatgct gcactacgag tttcctcctt 1350
atgcaactaa tgaaattggc aaagtcactg gtttaaatag aagagaactt 1400
gggcatggtg ctcttgctga gaaagctttg tatcctgtta ttcccagaga 1450
ttttcctttc accataagag ttacatctga agtcctagag tcaaatgggt 1500
catcttctat ggcatctgca tgtggcggaa gtttagcatt aatggattca 1550
ggggttccaa tttcatctgc tgttgcaggc gtagcaatag gattggtcac 1600
caaaaccgat cctgagaagg gtgaaataga agattatcgt ttgctgacag 1650
atatttggg aattgaagat tacaatgtga catggacttc aaaatagctg 1700
gcacttaata aaggaataac tgcattacag gctgatatta aattacctgg 1750
aataccaata aaaattgtga tggaggctat tcaacaagct tcagtggcaa 1800
aaaaggagat attacagatc atgaacaaaa ctatttcaaa acctcgagca 1850
tctagaaaag aaaatggacc tgttgtagaa actgttcagg ttccattatc 1900
aaaacgagca aaatttgttg gacctggtgg ctataactta aaaaaacttc 1950
aggctgaaac aggtgtaact attagtcagg tggatgaaga aacgttttct 2000
```

Fig. 2G

```
gtatttgcac caacacccag tgctatgcat gaggcaagag acttcattac 2050
tgaaatctgc aaggatgatc aggagcagca attagaattt ggagcagtat 2100
ataccgccac aataactgaa atcagagata ctggtgtaat ggtaaaatta 2150
tatccaaata tggctgcggt actgcttcat aacacacaac ttgatcaacg 2200
aaagattaaa catcctactg ccctaggatt agaagttggc caagaaattc 2250
aggtgaaata ctttggacgt gacccagccg atggaagaat gaggctttct 2300
cgaaaagtgc ttcagtcgcc agctacaacc gtggtcagaa ctttgaatgc 2350
agaagtagta ttgtaatggg agaaccratt tccagtcatc atctaattct 2400
cagtgatttt ttttttttaa agagaattct agaattctat tttgtctagg 2450
gtgatgtgct gtagagcaac attttagtag tatcttccat tgtgtagatt 2500
tctatataat ataaatacat tttaattatt tgtactaaaa aaaaaaaaaa 2550
aaaactcgag agtacttcta gagcgggccg cgggcccatc gattttccac 2600
ccggggggggt accaggtaag tgtcccggct cacc   SEQ ID NO: 10  2634
```

Fig. 2H 5.31 5' end

```
ggnnnntttg tttatnacac nccagctcga aattaaccct cactaaaggg    50
aacaaaagct ggagctcgcg cgcctgcagg tcgacactag tggatccaaa   100
gaattcggca cgaggtgtta ccagtgccca tcaggtgcct gccgtctctt   150
ctgtgtcaca cacagccctg tatactcctc cacctgagat acctaccact   200
gtcctcaaca ttccccaccc atcagtcatt tcctctccac ttctcaagtc   250
cttgcactct gctggacccc cgctccttgc tgttactgca gctcctccag   300
cccagcccct tgccaaggta tgatctgtgg atttcctctg ggcagcaggg   350
aggcaagggt cttaagtaaa gtgggcttgg agtgacaggt tccctatctt   400
gtttctttct gcagaaaaaa ggcgtaaagc ggaaagcaga tactaccacc   450
cctacaccta cagccatctt ggctcctggt tctccagcta gccctcctgg   500
gagtcttgag cctaaggcag cacggcttcc cctatgcgta gagagagtgg   550
tcgcccatca agccccacg  caaagacttn ctgactctan caacaacacc   600
agactctaag aaaggaaagc tttagaacag ttaaacattg caatggattt   650
tgangagtac tctctaanaa cat                                673
                                              SEQ ID NO: 11
```

5.31 3' end

```
ttgaaaataa tgatgggagt tttttgtcat gtgtgtgcaa ctcaacgagg    50
tctcctgtct gacagtgtaa attggagcta tatcacttgg gggctgggag   100
tagggcctgt ttatcagcat agttttgagt ttggcctctt tctaggatga   150
tttgagttcc gttatgccaa gatgccagat gaaccactag aaccagggcc   200
tttaccagtc tctactgcca tgccccctgg cttggccaaa tcgtcttcag   250
agtcctccag tgaggaaagt agcagtgaga gctcctctga ggaagaggag   300
gaggaagatg aggaggacga ggaggaagaa gagagtgaac ctcagactca   350
gaggaagaaa gggctcatcg cttagcagaa ctacaggaac aggtattttg   400
tcactcttga aagttttat  tgggtaagag gttcatgccc tttgtcctca   450
ttttttcttc ttgttatttt atctttattt acttttttca cttcatgttt   500
tttttccttt agcttcgggc agtacatgaa caactggctg ctctgtccca   550
gggtccaata tccaagccca agaggaaaaa aaaaaaaaa  aaa           593
                                              SEQ ID NO: 12
```

Fig. 21

MELANOMA ANTIGENS AND METHODS OF USE

CROSS-REFERENCE TO RELATED APPLICATION

This non-provisional patent application claims benefit of provisional patent application U.S. Ser. No. 60/160,042 filed Oct. 18, 1999, now abandoned.

FEDERAL FUNDING LEGEND

This invention was produced in part using funds obtained through grant 5R21CA78489 from the National Institute of Health. Consequently, the federal government has certain rights in this invention.

BACKGROUND OF THE INVENTION

1. Field of the Invention

The present invention relates generally to the field of cancer. More specifically, the present invention relates to antigens specific for melanoma carcinomas.

2. Description of the Related Art

Several methods have been employed to isolate and clone tumor-associated antigens, and in general, these methods have relied upon the ability of the antigens to stimulate cytolytic T cells (1–4). These methods involve demanding techniques, including extensive manipulation and expansion of cytolytic T cells.

Furthermore, it is becoming increasingly apparent that tumor-bearing individuals also develop serological immune responses to tumor antigens. Antibodies directed towards mutated cellular genes have been described, including those reactive with mutant p53 (5, 6) and ras (7). In addition, humoral immune responses to non-mutated, aberrantly expressed tumor antigens, such as erbB-2 (8) and cathepsin D (9), have been reported.

The presence of humoral immunity to many known tumor-associated antigens suggests its use for identification of novel tumor-associated antigens. The feasibility of this strategy was demonstrated in a study by Pfreundschuh and coworkers (10, 11) who screened tumor-derived cDNA libraries with autologous patient sera and identified two known tumor antigens as well as several novel, putative tumor antigens. This technology, termed SEREX, for serological identification of antigens by recombinant expression cloning, has since been applied by many groups and has led to the substantial expansion of known tumor antigens (12).

Thus, the prior art is deficient in additional novel antigens specific to melanomas. The present invention fulfills this long-standing need and desire in the art.

SUMMARY OF THE INVENTION

Herein, the SEREX approach was used to identify melanoma antigens in patients undergoing active immunotherapy. The primary goal of identifying novel melanoma antigens is to expand the potential targets for immunotherapy. In addition, characterization of these proteins has the potential to impact on diverse areas of melanoma research including detection, diagnosis and staging, characterization of the genetic changes associated with tumorigenesis, and the principles of immune activation and tumor cell rejection.

Novel melanoma tumor-associated antigens may be useful for detection, diagnosis, and staging of melanomas. Novel melanoma tumor-associated antigens may also be useful for monitoring to detect recurrence and metastatic disease and to monitor disease burden (e.g., proteins expressed on the cell surface may provide targets for monitoring, i.e., via detection and imaging of tumors). Novel tumor-associated antigens may additionally be useful as targets for immunotherapy and intervention strategies.

One object of the present invention is to provide elanoma tumor-associated antigens and methods of using the elanoma tumor-associated antigens.

In one embodiment of the present invention, there is provided DNA encoding a melanoma tumor-associated antigen selected from the group consisting of: (a) isolated DNA as shown in SEQ ID Nos. 1–12; (b) isolated DNA which is complementary to isolated DNA of (a) above; and (c) isolated DNA differing from the isolated DNAs of (a) and (b) above in codon sequence due to the degeneracy of the genetic code.

In another embodiment of the present invention, there is provided an isolated and purified melanoma tumor-associated antigen coded for by the DNA disclosed herein.

In another embodiment of the present invention, there is provided a method for detecting mRNA coding for a melanoma tumor-associated antigen in a sample, comprising the steps of: (a) contacting a sample with an oligonucleotide probe having a sequence such as SEQ ID Nos. 1–12; and (b) detecting binding of the probe to the mRNA coding for a melanoma tumor-associated antigen in the sample.

In yet another embodiment of the present invention, there is provided a kit for detecting mRNA coding for a melanoma tumor-associated antigen, comprising: an oligonucleotide probe having a nucleotide sequence shown in SEQ ID Nos. 1–12. The kit may further comprises: a label with which to label the probe; and means for detecting the label.

In still yet another embodiment of the present invention, there is provided a method of detecting a melanoma tumor-associated antigen in a sample, comprising the steps of: (a) contacting a sample with an antibody specific for a melanoma tumor-associated antigen or a fragment thereof encoded by the DNA disclosed herein; and (b) detecting binding of the antibody to the melanoma tumor-associated antigen in the sample.

In another embodiment of the present invention, there is provided a kit for detecting a melanoma tumor-associated antigen, comprising: an antibody specific for a melanoma tumor-associated antigen or a fragment thereof encoded by the DNA disclosed herein. The kit may further comprise means to detect the antibody.

In another embodiment of the present invention, there is provided an antibody specific for a melanoma tumor-associated antigen or a fragment thereof encoded by the DNA disclosed herein.

In still yet another embodiment of the present invention, there is provided a method of screening for compounds that inhibit the activity of a melanoma tumor-associated antigen, comprising the steps of: (a) contacting a sample with a compound, wherein the sample comprises a melanoma tumor-associated antigen encoded by the DNA disclosed herein; and (b) assaying for activity of the melanoma tumor-associated antigen. Generally, a decrease in the melanoma tumor-associated antigen activity in the presence of the compound relative to the melanoma tumor-associated antigen activity in the absence of the compound is indicative of a compound that inhibits the activity of the melanoma tumor-associated antigen.

In another embodiment of the present invention, there is provided a method of inhibiting the growth of a melanoma tumor in an individual, comprising the steps of: (a) treating an individual with a therapeutic compound, wherein the therapeutic compound comprises a thereapeutic moiety and a targeting moiety, wherein the targeting moiety recognizes a melanoma tumor-associated antigen encoded by the DNA disclosed herein; wherein the therapeutic compound inhibits the growth of the melanoma tumor in the individual.

In another embodiment of the present invention, there is provided a cancer vaccine composition, comprising a vector capable of expressing a DNA molecule such as SEQ ID Nos. 1–12, and an appropriate adjuvant.

In another embodiment of the present invention, there is provided a method of vaccinating an individual against cancer, comprising the step of: (a) administering to the individual a vector capable of expressing a DNA molecule such as SEQ ID Nos. 1–12, wherein said expression elicits an immune response specific towards a melonoma-specific antigen, thereby inducing immune-mediated destruction of melanoma cells.

In another embodiment of the present invention, there is provided a method of inhibiting the growth of a melanoma tumor, comprising the steps of: (a) administering to an individual a cancer vaccine comprising a vector expressing a DNA such as SEQ ID Nos. 1–12, wherein administration of said vaccine induces an immune response, thereby inhibiting the growth of a melanoma tumor.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIGS. 2A–I show the 5' and 3' sequences of clone 3.1 (FIG. 2A); clone 3.14 (FIG. 2B); clone 3.3T (FIG. 2C); clone 5.17 (FIG. 2D); clone 5.31 (FIG. 2I); and complete sequence of clone 5.23 (FIGS. 2E and 2F); clone 5.28 (FIGS. 2G and 2H).

DETAILED DESCRIPTION OF THE INVENTION

Figure 1:
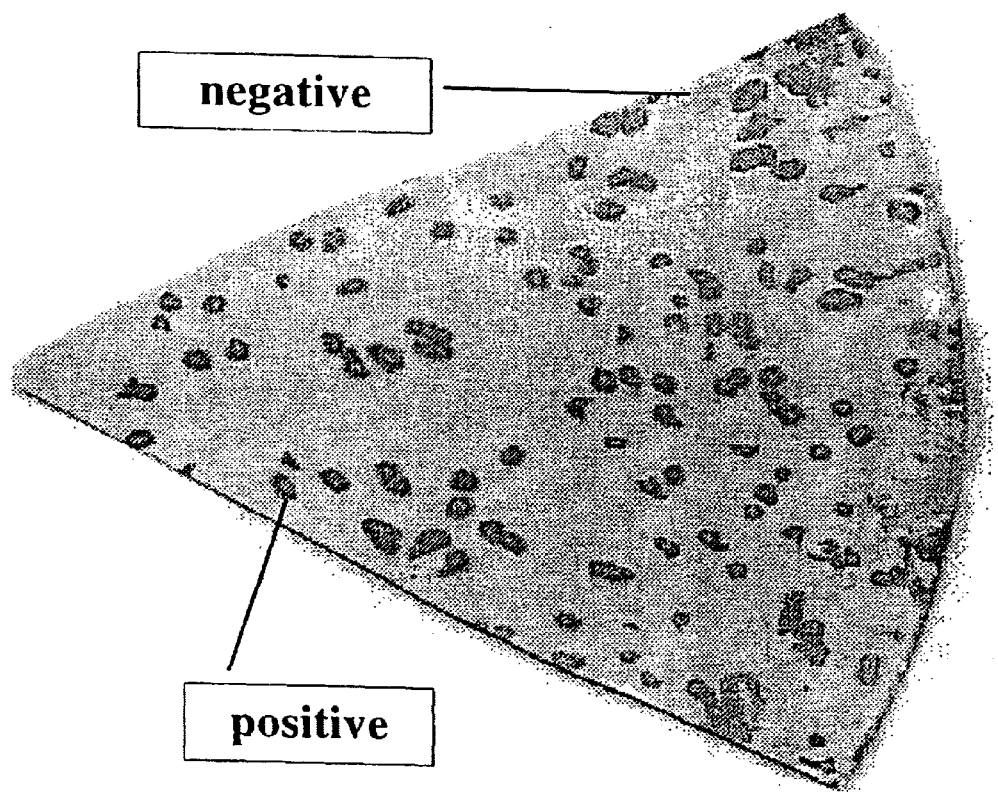
FIG. 1 shows an example of a colony lift assay with a purified positive clone. Clone 3.1 was plated in a 50:50 mix with a negative control phage. Filters were lifted from the plates, incubated with serum from patient 1, and reactive plaques were detected with a labeled secondary antibody. Dark circles represent the positive plaques for clone 3.1, while negative plaques are not detected.

The primary goal in identifying novel melanoma antigens is to expand the potential targets for immunotherapy. In addition, characterization of tumor antigens may impact diverse areas of melanoma research, including detection, diagnosis and staging, characterization of the genetic changes associated with tumorigenesis, and the principles of immune activation and tumor cell rejection.

The tumor-associated antigens of the present invention may be useful for detection, diagnosis, and staging of melanoma. Detection and diagnosis of melanoma is currently based on visual identification of melanoma lesions, while staging is based on depth of the lesion at the time of diagnosis. While these visual guidelines have proven useful, the use of additional marker proteins and molecular characterization of melanoma lesions may provide information useful in more accurately defining the clinical course of the disease.

The tumor-associated antigens of the present invention may also be useful for disease monitoring. Metastatic melanoma can spread to a variety of sites. The identification of the tumor-associated antigens of the present invention may allow recurrence and metastatic disease to be detected and disease burden monitored (e.g., by imaging an antigen-targeted melanoma cell).

The tumor-associated antigens of the present invention may further be useful as targets in immunotherapy. Several immunotherapy approaches directed towards melanoma cancers are currently under development. The tumor-associated antigens of the present invention will provide additional and specific therapeutic targets for intervention.

The SEREX approach has been used herein to identify novel melanoma antigens in patients undergoing active immunotherapy.

The present invention is directed towards a DNA encoding a melanoma tumor-associated antigen selected from the group consisting of: (a) isolated DNA having a sequence shown in SEQ ID Nos. 1–12; (b) isolated DNA which is complementary to the isolated DNA of (a) above; and (c) isolated DNA differing from the isolated DNAs of (a) and (b) above in codon sequence due to the degeneracy of the genetic code.

The present invention is also directed towards a vector comprising the DNA disclosed herein and regulatory elements necessary for expression of the DNA in a cell, wherein the DNA encodes a melanoma tumor-associated antigen. Also included in the present invention is a vector in which the DNA is positioned in reverse orientation relative to the regulatory elements such that a melanoma tumor-associated antigen antisense mRNA is produced. Further provided are host cells transfected with the above-described vector expressing a melanoma tumor-associated antigen. Representative host cells are bacterial cells, mammalian cells, plant cells and insect cells, more preferably, the bacterial cell is *E. coli*.

The present invention is additionally directed towards an isolated and purified melanoma tumor-associated antigen coded for by DNA selected from the group consisting of: (a) isolated DNA selected from the group consisting of SEQ ID Nos. 1–12; (b) isolated DNA which is complementary to the isolated DNA of (a) above; and (c) isolated DNA differing from the isolated DNAs of (a) and (b) above in codon sequence due to the degeneracy of the genetic code.

The present invention is further directed towards a method for detecting mRNA coding for a melanoma tumor-associated antigen in a sample, comprising the steps of: (a) contacting a sample with an oligonucleotide probe having a nucleotide sequence shown in SEQ ID Nos. 1–12; and (b) detecting binding of the probe to the mRNA coding for a melanoma tumor-associated antigen in the sample.

The present invention is also directed towards a kit for detecting mRNA coding for a melanoma tumor-associated antigen, comprising: an oligonucleotide probe having a nucleotide sequence such as SEQ ID Nos. 1–12. The above-described kit may further comprise a label with which to label the probe; and means for detecting the label.

The present invention is still further directed towards a method of detecting a melanoma tumor-associated antigen in a sample, comprising the steps of: (a) contacting a sample with an antibody specific for a melanoma tumor-associated antigen or a fragment thereof encoded by the DNA disclosed herein; and (b) detecting binding of the antibody to the melanoma tumor-associated antigen in the sample.

The present invention is additionally directed towards a kit for detecting a melanoma tumor-associated antigen, comprising: an antibody specific for a melanoma tumor-associated antigen or a fragment thereof encoded by the DNA disclosed herein. The above-described kit may further comprise means to detect the antibody.

The present invention is further directed towards an antibody specific for a melanoma tumor-associated antigen or a fragment thereof encoded by the DNA disclosed herein.

The present invention is also directed towards a method of screening for compounds that inhibit the activity of a melanoma tumor-associated antigen, comprising the steps of: (a) contacting a sample with a compound, wherein the sample comprises a melanoma tumor-associated antigen encoded by the DNA disclosed herein; and (b) assaying for activity of the melanoma tumor-associated antigen. Typically, a decrease in the melanoma tumor-associated antigen activity in the presence of the compound relative to the melanoma tumor-associated antigen activity in the absence of the compound is indicative of a compound that inhibits the activity of the melanoma tumor-associated antigen.

The antigens reported herein may play a role in signaling growth, activating the cell cycle, down-regulating inhibitors of growth and/or promoting metastatic spread. Alternatively, the antigens reported herein may normally be expressed in melanocytes and may or may not have a direct role in tumorigenesis.

The present invention is also directed towards a method of inhibiting the growth of a melanoma tumor in an individual, comprising the steps of: (a) treating an individual with a therapeutic compound, wherein the therapeutic compound comprises a thereapeutic moiety and a targeting moiety, wherein the targeting moiety recognizes a melanoma tumor-associated antigen encoded by the DNA disclosed herein; wherein the therapeutic compound inhibits the growth of the melanoma tumor in the individual. Preferred targeting moieties are an antibody or fragment thereof, or a ligand, while preferred therapeutic moieties are a therapeutic gene or protein, a toxin, a radiolabel or a virus.

The present invention is also directed toward a cancer vaccine composition, comprising a vector capable of expressing a DNA molecule having a sequence shown in SEQ ID Nos. 1–12, and an appropriate adjuvant.

The present invention is further directed toward a method of vaccinating an individual against cancer, comprising the steps of: (a) administering to the individual a vector capable of expressing a DNA molecule shown in SEQ ID Nos. 1–12, wherein expression elicits an immune response which is specific towards a melonoma-specific antigen, thereby inducing immune-mediated destruction of melanoma cells. Typically, the individual is at risk of getting cancer, suspected of having cancer or has cancer.

The present invention is also directed toward a method of inhibiting the growth of a melanoma tumor, comprising the steps of: (a) administering a cancer vaccine to an individual comprising a vector expressing a DNA such as SEQ ID Nos. 1–12, wherein administration of the vaccine induces an immune response, thereby inhibiting the growth of a melanoma tumor.

It will be apparent to one skilled in the art that various substitutions and modifications may be made to the invention disclosed herein without departing from the scope and spirit of the invention.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (2nd Ed.)", (1989); "DNA Cloning: A Practical Approach," Volumes I and II (D.N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R.I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. DNA structure is discussed herein according to the normal convention of showing only the sequence in the 5' to 3' direction along the nontranscribed strand of DNA (i.e., the strand having a sequence homologous to the mRNA).

A "vector" is a replicon, such as plasmid, phage viral genome or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in and/or regulate DNA synthesis. An "expression control sequence" or "regulatory elements necessary for expression" are DNA sequence(s) that control and regulate the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNAs from eukaryotic mRNA, genomic DNA sequences from eukaryotic (e.g., mammalian) DNA, and even synthetic DNA sequences. A coding sequence may alternatively be transcribed in the opposite orientation (i.e., the nontranscribed strand is used as the template) to produce an antisense RNA molecule. An antisense RNA is complementary to an mRNA molecule produced from the transcribed strand.

A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed, usually spliced-out, sequence.

Transcriptional and translational regulatory sequences, such as promoters, enhancers, polyadenylation signals, terminators, and the like, provide for expression of a coding sequence in a host cell. A "cis-element" is a nucleotide sequence, also sometimes termed a "consensus sequence" or "motif", that interacts with proteins that regulate expression of a specific gene locus. A "signal sequence" can also be included with the coding sequence. This sequence encodes a signal peptide, N-terminal to the polypeptide, that communicates with the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as consensus sequences responsible for binding of RNA polymerase. Eukaryotic promoters often, but not always, contain "TATA" boxes and "CAT" boxes. Prokaryotic promoters typically contain the −10 and −35 consensus sequences, as well as Shine-Dalgarno sequences for ribosome binding.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally (as in a purified restriction digest) or produced synthetically, which is capable of acting as a point of initiation when placed under conditions in which synthesis of a primer extension product, which is complementary to a nucleic acid strand, is induced, i.e., in the presence of nucleotides and a polymerizing agent such as a DNA polymerase, and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending upon the complexity of the target sequence, the oligonucleotide primer typically contains 15–25 or more nucleotides, although it may contain fewer nucleotides.

Primers are selected to be "substantially" complementary to a strand of a particular target DNA sequence. This means that the primers must be sufficiently complementary to hybridize with their respective strands under the appropriate conditions. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence to hybridize therewith and thereby initiate synthesis of the extension product.

As used herein, the terms "restriction endonucleases" and "restriction enzymes" refer to enzymes which cut double-stranded DNA at or near a specific nucleotide sequence. "Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning", "cloning" and "genetic engineering". The product of these manipulations results in a "recombinant" or "recombinant molecule".

A cell has been "transformed" or "transfected" with exogenous or heterologous DNA when such DNA has been introduced into the cell. The transforming DNA may or may not be integrated (covalently linked) into the genome of the cell. In prokaryotes, yeast, and mammalian cells for example, the transforming DNA may be maintained on an replicative episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived (by mitosis) from a single cell or ancestor. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes, but also eukaryotes, such as yeast cells, plant cells and animal cells. A recombinant DNA molecule or gene can be used to transform a host using any of the techniques commonly known to those of ordinary skill in the art. Prokaryotic hosts may include *E coli, S. tymphimurium, Serratia marcescens* and *Bacillus subtilis*. Eukaryotic hosts include yeasts such as *Pichia pastoris*, mammalian cells and insect cells, and plant cells, such as *Arabidopsis thaliana* and *Tobaccum nicotiana*.

As used herein, "fragment," as applied to a polypeptide, will ordinarily be at least 10 residues, more typically at least 20 residues, and preferably at least 30 (e.g., 50) residues in length, but less than the entire, intact sequence. Fragments can be generated by methods known to those skilled in the art, e.g., by enzymatic digestion/cleavage of naturally occurring or recombinant protein, by recombinant DNA techniques using an expression vector that encodes a defined fragment, or by chemical synthesis. The ability of a candidate fragment to exhibit an enzyme characteristic (e.g., binding to a specific antibody, or exhibiting enzymatic or catalytic activity) can be assessed by methods described herein. Purified fragments or antigenic fragments can be used to generate new regulatory enzymes using multiple functional fragments from different enzymes, as well as to generate antibodies, by employing standard protocols known to those skilled in the art.

Generally speaking, antibodies for use in these aspects of the present invention will preferably recognize antigens that are preferentially, or specifically, expressed by melanoma tumor cells. Such antibodies will also preferably exhibit properties of high affinity, such as exhibiting a $K_d$ of <200 nM, and preferably, of <100 nM, and will not show significant reactivity with normal tissues, such as tissues from heart, kidney, brain, liver, bone marrow, colon, breast, prostate, thyroid, gall bladder, lung, adrenals, muscle, nerve fibers, pancreas, skin, or other life-sustaining organ or tissue in the human body. These tissues are important for the purposes of the present invention from the standpoint of low reactivity with the antibody. The term "reactivity," as used herein, refers to an antibody or antibody fragment that, when applied to the particular tissue under conditions suitable for immunohistochemistry, will elicit staining only in positive cells and not negative cells. Particularly promising antibodies contemplated for use in the present invention are those having high reactivity specific to the melanoma tumor.

A standard Northern blot assay can be used to ascertain the relative amounts of mRNA in a cell or tissue obtained from tissue in accordance with conventional Northern blot hybridization techniques known to those persons of ordinary skill in the art. Alternatively, a standard Southern blot assay may be used to confirm the presence and the copy number of a gene in accordance with conventional Southern blot hybridization techniques known to those of ordinary skill in the art. Both the Northern blot and Southern blot use a hybridization probe, e.g., radiolabelled cDNA, either containing the full-length, single stranded DNA or a fragment of the DNA sequence at least 20 (preferably at least 30, more preferably at least 50, and most preferably at least 100 consecutive nucleotides in length). The oligonucleotide hybridization probe can be labelled by any of the many different methods known to those skilled in this art. Conditions for Northern and Southern hybridizations, i.e., stringency, can be determined for that particular system empirically and/or experimentally, and defining appropriate hybridization conditions is well within the skill of the art. See, e.g., Maniatis et al., supra; DNA Cloning, Vols. I & II, supra; Nucleic Acid Hybridization, supra.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID Nos. 1–12 or which encodes an alternative splice variant of SEQ ID Nos. 1–12.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^3$H, $^{14}$C, $^{32}$P, $^{35}$S $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and routinely utilized. The preferred enzymes are peroxidase, β-glucuronidase, β-D-glucosidase, β-D-galactosidase, urease, glucose oxidase plus peroxidase and alkaline phosphatase, etc. U.S. Pat. Nos. 3,654,090, 3,850,752, and 4,016,043 are referred to by way of example for their disclosure of alternate labeling material and methods.

By "degeneracy of the genetic code" is meant that some amino acids are specified by more than one codon. Accordingly, a single protein sequence could be coded for by multiple DNA sequences due to the degeneracy of the genetic code.

As used herein, "cancer vaccine" refers to a therapeutic vaccine consisting of a vector encoding an antigenic protein or a peptide fragment thereof. Immunization of an individual with such a vaccine is meant to induce an immune response to the protein or peptide, and is directed towards a method of inhibiting growth or promoting destruction of the melanoma tumor in the individual.

As used herein, "immunotherapy", as used in the context of cancer therapy, refers to a therapeutic method achieved by manipulation of an individual's immune system to inhibit growth or promote destruction of a tumor.

As used herein, "antigen" generally refers to a protein or polypeptide which can, in certain formulations or settings, be recognized by the immune system and elicit an immune response. Although carbohydrate moieties may also act as antigens, as used herein, antigens are defined as proteins or polypeptides which may or may not be modified post-translationally.

As used herein, "tumor-associated antigen" refers to an antigen which is associated with tumor cells. Such proteins need not be expressed exclusively in or on tumor cells. Generally, tumor-associated antigens are fetal proteins aberrantly expressed in tumor cells, mutated cellular proteins which are antigenic due to the mutation, viral proteins expressed in tumor cells, normal cellular proteins highly expressed in the tumor compared to normal tissue, or normal cellular proteins which are mislocalized.

As used herein, "melanoma antigen" refers to an antigen which is expressed in melanoma cells, however, expressed need not be limited to only melanoma cells.

As used herein, "polymerase chain reaction" or "PCR" refers to an enzymatic reaction using primers specific for a DNA or cDNA sequence which results in amplification of the specified sequence.

The following examples are given for the purpose of illustrating various embodiments of the invention and are not meant to limit the present invention in any fashion:

EXAMPLE 1

Patient Poplulation and Clinical Trial

Nine patients with advanced stage melanoma were enrolled in a Phase Ib clinical trial (NCI Protocol T97-0005) of intratumoral injection of a recombinant canarypox virus encoding the human interleukin-12 (IL-12) gene. The recombinant virus was provided by Pasteur Merieux Connaught through an agreement with the National Cancer Institute. Patients were injected with the recombinant virus encoding IL-12 on days 1, 4, 8, and 11 and serum was collected on days 0, 18 and 43.

EXAMPLE 2 cDNA Library Construction

A cDNA expression library derived from the melanoma cell lines MEL888 and MEL624 (kindly provided by S. Rosenberg, National Cancer Institute) was synthesized in the 1-ZAP Express vector (Stratagene). Briefly, total RNA was isolated from the cells using the RNA-STAT™ reagent (TelTestB), according to the manufacturer's directions. mRNA was isolated using a 5'→3' mRNA isolation kit. Five to seven micrograms of mRNA was reverse transcribed using an oligo dT primer with an internal XhoI site. After second strand synthesis, EcoRI adapters were added by ligation. The cDNA was passed through a size exclusion column (Pharmacia) which eliminates cDNAs smaller than 400 bp in size and the cDNA fragments cloned into the λZAPEXPRESS™ vector, packaged according to the manufacturer's instructions, and used to infect *E.coli* cells. As a preliminary characterization of the library, inserts from twenty-five randomly selected recombinant plaques were PCR amplified using T3 and T7 primers to determine insert size ranges (0.5 to 3.0 kb). The library contained $6.8 \times 10^6$ primary recombinants.

EXAMPLE 3

Immunoscreening

Table 1 shows isolated clones screened for reactivity with all patients from the study. A cDNA expression library was generated from the melanoma cell lines MEL888 and MEL624, and serum from two individuals (patients one and two) was diluted to 1:250, mixed in equal volume and used to screen the library. Recombinant plaques were plated at a density of approximately 25,000 plaques per 150 mm plate, and a total of approximately 200,000 plaques were screened. After a four hour incubation of the plates at 37° C., protein expression was induced by incubation of the plates with nitrocellulose filters saturated with isopropyl β-D-thiogalactoside (IPTG) overnight. Filters were blocked with 1% BSA in Tris-buffered saline (TBS; 20 mM Tris (pH 7.5), 150 mM NaCl) and screened with patient sera. Primary sera is preabsorped with *E coli* phage lysate (Stratagene) and diluted 1:250 for screening. After incubating filters with diluted sera, the filters were washed with TBST (TBS with 0.05% Tween 20 [Sigma]) and incubated with alkaline phosphatase-conjugated goat anti-human IgG (H+L) antibodies (Jackson Labs) at a dilution of 1:5,000 for 1 hour at room temperature. After washing, an NBT/BCIP calorimetric assay was used to identify positive clones. Positive plaques were purified to clonality for further study.

Isolated clones (FIG. 1) were then screened for reactivity against sera from nine patients with advanced stage melanoma who were intratumorally injected with a recombinant canarypox virus encoding the human interleukin-12 (IL-12) gene. Patients were injected with the recombinant virus encoding IL-12 on days 1, 4, 8, and 11 and serum was collected on days 0, 18 and 43. Confirmed immunoreactive plaques were evaluated for reactivity with serum from ten normal individuals. Only those plaques which were not reactive with ten normal sera were processed further.

TABLE 1

| | Patients Day 43 | | | | | | | | | Patient 1 | |
|---|---|---|---|---|---|---|---|---|---|---|---|
| | 1 | 2 | 3 | 4 | 5 | 6 | 7 | 8 | 9 | Day 18 | 0 |
| 3.1 | + | − | − | − | − | − | − | − | − | + | − |
| 3.14 | + | − | − | − | − | − | − | − | − | + | − |
| 5.16 | + | − | − | − | − | − | − | − | − | + | − |
| 5.17 | + | + | − | − | − | − | − | − | − | + | − |
| 5.23 | + | − | − | − | − | − | − | − | − | + | − |
| 5.28 | + | − | − | − | − | − | − | − | − | + | − |
| 5.31 | + | − | − | − | − | − | − | − | − | + | − |
| 3.3T | − | − | − | − | + | − | − | − | + | n/a | n/a |

Isolated clones were screened for reactivity with all patients from the study.

EXAMPLE 4

Isotype Analysis

Upon plaque purification, the isotype of the reactive antibodies were determined using human isotype specific antibodies (Southern Biotech), according to the recommended procedure. Isotype analysis demonstrated the presence of predominantly IgG antibodies, consistent with a mature, $T_n$-dependent immune response.

EXAMPLE 5

Isolation of Plasmid DNA and DNA Sequence Analysis

Plasmid DNA containing cDNA inserts of interest were isolated from purified plaques by in vivo excision using a helper phage system (EXASSIST™, Stratagene). For single clone excision, approximately $10^5$ phage particles were used to infect XL-1-Blue MRF cells in the presence of the helper phage and the cells were incubated for 3 hours at 37° C. To isolate the excised phagemid which are packaged as filamentous phage particles, the culture was heated to 70° C. for 20 min, spun at 1000×g for 15 min and the supernatant collected. These phage were used to infect XLOR™ cells (Stratagene) and the cells were plated on selective media. These cells do not permit growth of the helper phage and only allow propagation of the phagemid. Single colonies were grown in liquid culture and DNA isolated by standard miniprep procedures.

Partial DNA sequence of each insert was determined using an automated DNA sequencer and vector specific primers. Partial DNA sequences were used in BLAST searches through the National Center for Biotechnology Information database to identify sequences which matched previously described genes or expressed sequence tags (ESTs) (Table 2).

TABLE 2

Melanoma tumor-associated antigen homology

| Clone & Identifier | Homology with: | Reference |
|---|---|---|
| 3.1 (SEQ ID No. 1 & 2) (=3.8 = 3.16) | KIAA0663 (GenBank Accession No. AB014563) | 13 |
| 3.14 (SEQ ID No. 3 & 4) | Drosophila disc large protein (GenBank Accession No. U13896) | 14 |
| 3.3T (SEQ ID No. 5 & 6) | Ubiquilin; DA41 (GenBank Accession No. AF176069, HRIHFB2157) | 15 |
| 5.17 (SEQ ID No. 7 & 8) | KIAA0555 (GenBank Accession No. AB011127) | 16 |
| 5.23 (SEQ ID No. 9) | EST:qu76c08.x1; NCI-CGAP-ES02 (GenBank Accession No. AI354862) | 17 |
| 5.28 (SEQ ID No. 10) | Various ESTs; Similarity with TR:G581223 | |
| 5.31 (SEQ ID No. 11 & 12) | RING3* (GenBank Accession No. X96670) | 18 |

*RING3 has been described by Matthew Scanlan at the Ludwig Institute for Cancer Research as a potential breast tumor antigen based on SEREX.

The positive clones, derived from plaques that bound sera from patients intratumorally injected with a recombinant virus expressing IL-12, represent putative antigens specific to melanoma tumors.

EXAMPLE 6

Uses

Novel tumor-associated antigens may be useful for detection, diagnosis, and staging of melanoma. Detection and diagnosis of melanoma is currently based on visual identification of melanoma lesions, while staging is based on depth of the lesion at the time of diagnosis. While these visual guidelines have proven quite useful, the use of additional marker proteins and the molecular characterization of melanoma lesions may prove more accurate in defining the clinical course of the disease.

Novel tumor-associated antigens may also be useful for disease monitoring. Metastatic melanoma can spread to a variety of sites. The identification of novel tumor antigens may allow recurrence and metastatic disease to be detected and disease burden monitored. Antigenic proteins expressed on the cell surface may provide targets for detection and imaging of metastatic disease.

Tumor-associated antigens may additionally be useful as novel targets for immunotherapy. Several immunotherapeutical approaches to melanoma are currently under development, and tumor-associated antigens may provide additional therapeutic targets for intervention.

The following references were cited herein:

1. van der Bruggen, P et al. *Science* 254:1643–1647, 1991.
2. Kawakami, Y et al. *Proc. Natl. Acad. Sci. USA* 91:3515–3519, 1994.
3. Toso, JF et al. *Cancer Res.* 56:16–20, 1996.
4. Robbins, PF et al. *Cancer Res.* 54:3124–3126, 1994.
5. Schlichtholz, B et al. *Cancer Res.* 52: 6380–6384, 1992.
6. Lubin, R et al. *Cancer Res.* 53:5872–5876, 1993.
7. Stauss, HJ *J Natl Cancer Inst.* 87:820–821, 1995.
8. Disis, ML et al. *Cancer Res.* 54:16–20, 1994.
9. Chinni S et al. *Clin Cancer Res.* 3:1557–1564, 1997.
10. Sahin, et al. *Proc. Natl Acad Sci.USA* 92:11810–11813, 1995.
11. Tureci, O et al. *Cancer Res* 56:4766–4772, 1996.
12. Old, LO & Chen, YT. *J. Exp. Med.* 187:1163–1167, 1998.
13. Ishikawa, K et al. *DNA Res.* 5:169–176, 1998.
14. Lu, RA et al. *Proc. Natl. Acad. Sci. USA* 91:9818–22, 1994.
15. Hanaoka, E et al. *J. Human Genet.* 45:188–191, 2000.
16. Ishikawa, K et al. *DNA Res.* 5:31–19, 1998.
17. Natl. Cancer Institute; Cancer Genome Anatomy Project.
18. Thorpe, KL et al. *Immunogenetics* 44:391–6, 1996.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated DNA encoding a melanoma tumor-associated antigen, said DNA is selected from the group consisting of:
   (a) isolated DNA having the sequence of SEQ ID NO. 3; and
   (b) isolated DNA differing from the isolated DNA of (a) in codon sequence due to the degeneracy of the genetic code.

2. A vector comprising the DNA of claim 1 and regulatory elements necessary for expression of said DNA in a cell.

3. An isolated host cell transfected with the vector of claim 2, said vector expressing a melanoma tumor-associated antigen.

4. The host cell of claim 3, wherein said cell is selected from group consisting of bacterial cells, mammalian cells, plant cells and insect cells.

5. The host cell of claim 4, wherein said bacterial cell is *E. coli*.

6. A kit for detecting mRNA coding for a melanoma tumor-associated antigen, comprising:
   an oligonucleotide probe specific for a melanoma tumor-associated antigen, wherein said probe consist of a DNA fragment of SEQ ID NO. 3.

7. The kit of claim 6, further comprising:
   a label with which to label said probe; and
   means for detecting said label.

* * * * *

SEQUENCE LISTING

```
<160> NUMBER OF SEQ ID NOS: 12

<210> SEQ ID NO 1
<211> LENGTH: 586
<212> TYPE: DNA
<213> ORGANISM: Unknown
<220> FEATURE:
<221> NAME/KEY: mat_peptide
<222> LOCATION: 5,8,17,38,45,68,95,465,470,472,476,506,507,
<222> LOCATION: 514,540,552,564,
<223> OTHER INFORMATION: 5' end of clone 3.1 encoding a melanoma
```

-continued tumor-associated antigen; n = unknown

<400> SEQUENCE: 1

| | | | | | |
|---|---|---|---|---|---|
| atggnatntg | tttgaancct | attttgaaac | cttgccanct | cgaantaacc | 50 |
| ctcataaggg | caacaaanct | ggagctcgcg | cgcctgcagg | tcganactag | 100 |
| tggttccaaa | gaattcggca | cgagcctaat | caaggagaag | actgctattt | 150 |
| ttttttctat | tccacatgta | ccaaaggcga | cagctgccca | ttccgtcact | 200 |
| gtgaagctgc | aataggaaat | gaaactgttt | gcacattatg | caagaaggg | 250 |
| cgctgttttc | gacaggtgtg | caggtttcgg | cacatggaga | ttgataaaaa | 300 |
| acgcagtgaa | attccttgtt | attgggaaaa | tcagccaaca | ggatgtcaaa | 350 |
| aattaaactg | cgctttccat | cacaatagag | gaccgatatg | ttgatggcct | 400 |
| tttcctacct | ccgagcaaaa | ctgtgttgcc | cactgtgcct | gagtcaccag | 450 |
| aagaggaaag | tgaangctan | cncaantttc | agttcaagct | ggaacaaaat | 500 |
| tggctnntcc | aatnccaaat | cccttcccct | taaacctggn | ggaaaccgtt | 550 |
| antgaaaagt | tagnaaattt | tcccgaaaat | tgttct | | 586 |

<210> SEQ ID NO 2
<211> LENGTH: 615
<212> TYPE: DNA
<213> ORGANISM: Unknown
<220> FEATURE:
<223> OTHER INFORMATION: 3' end of clone 3.1 encoding a melanoma
  tumor-associated antigen

<400> SEQUENCE: 2

| | | | | | |
|---|---|---|---|---|---|
| cgcctggaaa | agggtaagta | acccagggac | ggagccttgg | gtaaagtgtg | 50 |
| tcatccccca | attggcccaa | cgtaagcagt | gagatgccgc | tgtgtcattg | 100 |
| ccgctgtgaa | cctcagtcca | caggtcctac | aggaccccca | gccaaaaagg | 150 |
| cagctgtggc | tgttgtcccg | cttgtcttga | ggcaaatcag | tcctgtgcct | 200 |
| gaagcagaaa | atcctagagc | agtcttgtgc | tgcctccaac | ccagtccttt | 250 |
| cagattcctc | accccagag | gtgtctggcc | ctcctcatcc | caatgagcat | 300 |
| gaaaactgcc | gactcagctt | tgcctcaaca | ggaaagcccc | cactcttgtg | 350 |
| gaggatgatt | tagaaacta | atatgggaga | tttcaggagg | caaattggaa | 400 |
| gctgagattg | acctggatct | gggaaaatga | aatgaccttt | gcttgagcta | 450 |
| tcaaaatgat | tatagctgaa | ggtggtagtg | aggacccttt | aaaaaaaaaa | 500 |
| tcgccaaaaa | ctggcttagt | ttcattattg | aactttacct | gagatgatct | 550 |
| tttttagtta | gaatttgccc | caatcaaaga | accttgaatt | atccaaaaaa | 600 |
| aaaaaaaaaa | aaaaa | | | | 615 |

<210> SEQ ID NO 3
<211> LENGTH: 574
<212> TYPE: DNA
<213> ORGANISM: Unknown
<220> FEATURE:
<221> NAME/KEY: mat_peptide
<222> LOCATION: 8,9,21,29,52,473,515,545,573
<223> OTHER INFORMATION: 5' end of clone 3.14 encoding a melanoma
  tumor-associated antigen; n = unknown

<400> SEQUENCE: 3

| | | | | | |
|---|---|---|---|---|---|
| ggggtatnnt | ttgaaccttc | nttctccant | taaccctcat | aagggaacaa | 50 |

```
anctggactc gcgcgcctgc aggtcgacac tagtggatcc aaagaattcg        100
gcacgagttt atcttagccg gaggacctgc tgatctaagt ggagagctca        150
gaaaaggaga tcgtattata tcggtaaaca gtgttgacct cagagctgct        200
agtcatgagc aggcagcagc tgcattgaaa aatgctggcc aggctgtcac        250
aattgttgca caatatcgac ctgaagaata cagtcgtttt gaagctaaaa        300
tacatgattt acgggagcag atgatgaata gtagtattag ttcagggtca        350
ggttttcaaa tggttcctga ggttttttgt tgttgtccgt gttgttactg        400
ttgttcttgt catcaggttt gattttggtc cttgcccttt ccttctagtt        450
ctccttttat taataggaaa ggnaggcaaa agcccccatt tatgtggggg        500
ggttttcccc ttaanacagc ttttcattcc acctggttct gcacntaaaa        550
ttggccccaa aatcttcatt ggng                                    574
```

<210> SEQ ID NO 4
<211> LENGTH: 528
<212> TYPE: DNA
<213> ORGANISM: Unknown
<220> FEATURE:
<223> OTHER INFORMATION: 3' end of clone 3.14 encoding a melanoma
      tumor-associated antigen

<400> SEQUENCE: 4

```
accgtgttga actaaaactt ttcgggccca ttttaaatg gggttttcag          50 ggcccgtttt caaaaggttc ctaaggtttt tgttgtgccc gggttgtaac        100
tggttgttct gtcatcaggt ttgattttgg gcccttgcc tttccttcta        150 gttctccttt tattaatagg aaggcaggca aaagccccat ttatgtggtg        200
ttttcccctc agacagcttt catccactgc tctgcactag aattgcacaa        250
atcttcatgg tgagcaattt taagaaatgt tagtaaaagg tagaaattat        300
ttcacaaatc agtttctctg gtccttcata ttaataataa tatttggctt        350
cccattgctc tttggagttg tttattaaat atgtgttttt gacaacctcc        400
tcattagttt cttaaatgag tactggtttg taaagaatta tcaacattat        450
ccattccatt tatgaagaag aggagaacag ctaataaact gtattgaaat        500
ccaaaaaaaa aaaaaaaaaa aaaaaaaa                                528
```

<210> SEQ ID NO 5
<211> LENGTH: 547
<212> TYPE: DNA
<213> ORGANISM: Unknown
<220> FEATURE:
<221> NAME/KEY: mat_peptide
<222> LOCATION: 4,5,26,183,216,223,231,250,252,271,315,342,351,
<222> LOCATION: 356,357,358,360,367,370,372,374,386,394,395,402,
<222> LOCATION: 409,416,420,421,435,444,461,467,482,493,495,499,
<222> LOCATION: 500,517,527
<223> OTHER INFORMATION: 5' end of clone 3.3T encoding a melanoma
      tumor-associated antigen; n = unknown

<400> SEQUENCE: 5

```
aggnnggagc actcagctcg aaattnaccc tcactaaagg gaacaaaagc         50
tggagctcgc gcgcctgcag gtcgacacta gtggatccaa agaattcggc        100
accaggaaat ccagaaatta gtcatatgtt gaataatcca gatataatga        150
gacaaacgtt ggaacttgcc aggaatccag cantgatgca ggagatgatg        200
```

```
aggaaccagg accganctttt gancaaccta naaagcatcc caggggggatn      250 tnatgcttta aggcgcatgt ncacagatat tcatgaacca atgctgagtg       300
ctgcacaaaa acaanttggg gggaaaccat ttgcttcctt gngaacaaat       350
natccnnngn ggaaggnagn cnanccttcc cgtccngaaa ttnnattcc        400 cntcccatnc cttggncccn naactcccaa atttntaaat ttcnacggcc       450
tgcacctggg ngggcantcg gttcctgcca gnggccttt ggnanatann        500 ctgccaaatt ggcccgngag agaactnttt tttcaacaca caaaatg          547
```

<210> SEQ ID NO 6
<211> LENGTH: 413
<212> TYPE: DNA
<213> ORGANISM: Unknown
<220> FEATURE:
<223> OTHER INFORMATION: 3' end of clone 3.3T encoding a melanoma
      tumor-associated antigen

<400> SEQUENCE: 6

```
ttttccgtga gaaacattca gttaaacaca ggggggggatc accagctaat      50 aaagggtatg ggtcccctca tacagcattt tgtttttaaa aaatggattt       100
atttttgtaa cgggtttaaa cttaaaaaac ccgcttatt tcatttgctt        150 tgggaattgg cgttaaacca accccaatta gccttttaag ggggctaaag       200
gggggtttcg gaatttttt tcggaggga ataaggaag gagatcttgc          250 attaatggat ttttaaaacc ccctttaaa gtgggggacc agattttgtc        300
ctgcatctgt ccagttattt gcttttaaa catagcctat ggtagtaatt        350
tatgtagaat aaaagcatta aaagaagca aatcatttgc tctctaaaaa       400
aaaaaaaaaa aaa                                              413
```

<210> SEQ ID NO 7
<211> LENGTH: 616
<212> TYPE: DNA
<213> ORGANISM: Unknown
<220> FEATURE:
<221> NAME/KEY: mat_peptide
<222> LOCATION: 4,5,11,453,481,498,501,531,552,568,569,571,572,
<222> LOCATION: 586,588,591,595,602,614
<223> OTHER INFORMATION: 5' end of clone 5.17 encoding a melanoma
      tumor-associated antigen; n = unknown

<400> SEQUENCE: 7

```
aggnntaggt naccctacta aagggaacaa aagctggagc tcgcgcgcct       50
gcaggtcgac actagtggat ccaaagaatt cggcacgagc cgactcggtc       100
acaaggaaaa tggattcagt ttgcatctct ccctccttta aacagcttct       150
ccgggtctca gcatggtatc aaagcttgaa agagagaaga ctcaagaagc       200
gaagaggatt cgtgagctgg agcagcgcaa gcacacggtg ctggtgacag       250
aactcaaagc caagctccat gaggagaaga tgaaggagct gcaggctgtg       300
agggagaacc ttatcaagca gcacgagcag gaaatgtcaa ggacggtgaa       350
ggtacgtgat ggaagaagat ccagaggctc aagtctgctc tctgtgctct       400
ccgcgacggc agcagtgacc aaagtaagga cagcgctacc attgaggccc       450
ggnaaggagg cccgaaacct gtttgaccca nacgcctaa gctttacngg        500 naaattgcgg acctgaaacg gccaaaagcc nggggccaa aggtttttgcc      550
```

```
antttgatcc caaggccnna nnttttatag tgggcntnga nggcnttatc          600
cncaaacctt taanat                                              616
```

<210> SEQ ID NO 8
<211> LENGTH: 510
<212> TYPE: DNA
<213> ORGANISM: Unknown
<220> FEATURE:
<223> OTHER INFORMATION: 3' end of clone 5.17 encoding a melanoma
      tumor-associated antigen

<400> SEQUENCE: 8

```
gtaccccga aaagggttta cccttaaggg caattgttcc cccccccct            50 aagggttcca aagttaagat tccccctgaa cggctaaggg ttttaaagcc         100
ttattcaagg tttcttactt gccagttcct accaaaccct gtaaaatctc         150
caataatgct gcatttaatg aaacatggta tatgtcaaat cagaagagaa         200
gaactataaa catatattgt gtaaagaaaa agttcagcaa tggaactagt         250
tttgcagatc aagcaaagat gtgtcttggg catggaacca aagttacaat         300
gaaatattca acccctgctg tgcagggggg tcatttttaat gtaacaccac         350 accccatgga aacactagtc ctgataataa acatcatttt aaaagatcaa         400
aacaaacaaa caaaaaaaac aagggtgggt ggggagtgaa gcacgaggaa         450
tacctatgaa gagctatttta caataaaatg tttcatttga aaaaaaaaa         500 aaaaaaaaa                                                      510
```

<210> SEQ ID NO 9
<211> LENGTH: 3512
<212> TYPE: DNA
<213> ORGANISM: Unknown
<220> FEATURE:
<221> NAME/KEY: prim_transcript
<223> OTHER INFORMATION: complete sequence of clone 5.23 encoding a
      melanoma tumor-associated antigen

<400> SEQUENCE: 9

```
ggacaacagc tggagctcgc gcgcctgcag gtcgacacta gtggatccaa           50
agaattcggc acgagagaaa gtaaggaaaa gttcagggta tagaaatagc          100
tattcagtga ctttgtattt ttacttgtgc tcttaagaac ctttattcat          150
gtaatgcaaa gtaatttgtg ttgaagttga acttgtgaga aaatatatag          200
tacctaatgc attctcattt ggaatatgtg atctgtagaa atggaaatat          250
ttttatttat tttactgttt ttataggagg ttcgtaaagt gaatgaaagc          300
atcaagataa tcacccattg agaaaatgtg ttgatacaat acttaaaaag          350
tgccctacag agtatcagga aaaatgggt aggaacatgg atgattatga           400
agattttgat gaaaagcata gtatctatcc agtgaaaaaa gtctggtaaa          450
actgccataa acaggggact tgctaatta taagtatttt actaatgatg           500
atttttaatt agacttctaa tcattgctca taaaaaagg aattttagt            550 gaatgtgtat ttaaaacttc ctttaatccc gtccttatca ttctttgaaa          600
tattttatct ctgtgtatac cagcaggggt attattggcg tttggggagg          650
gagaattctt cactgagcat aactgttaca ttatataaaa ctgttacatc          700
attttggaac attaatattc tcagcctgac ccagtaaatg ccctagcact          750
```

-continued

```
ttcccattgt tatgacaatc caaacatgct ccctagtgga gagttgaacc       800
actgttggat cagaacactg ccaggtctac ccccattctc ttttttaggt       850
gatttattca gttcagagac accgtcgaac tcaagtacaa tggcagattc       900
ttttggaaca agcattttat ctagaagatg tagcaaaaaa tgaaactagt       950
gctactcatc agtttgttca cacctttcaa tcgccagagc cagaaaatcg      1000
atttatccaa tattttata atcctacatt tggtatgtaa tttgatataa      1050
atttcaaact ttaatgatga aaagttttct gtagaaagaa gttatgtatt      1100
ttcaccaatg caaagttgaa ttttatttgt attatttgat ttataccatg      1150
tgatattaag tatctggtaa catttcccca aaataactgt tttacttatc      1200
atataacata taatccatca gtttccactg ttacttcaca aataataaaa      1250
attctattaa aaaacatgta tacatcaagc atattttta taatgcataa      1300
tatatacaat tatgcattgc ttaatgactg ggattactct gagaaatgta      1350
ttgttaggca atttcatcac tgcatgagca tcatagggta tgtactaaac      1400
ctagatggta tagtacaggt aggcaaatat gggtattggc ttattactcc      1450
taaggctaca aaacctatac agcatggtta ctgtacctga aagtggtagg      1500
cagttgtaca ccagggtttt tggtttttaa acttgaaaaa tattttaaa      1550
agccgttgta attttgggg atcacccttt ttttgcaccc tctttggccg      1600
ggaggtgtat tgaccccta gtcctttaaa aatagaaatt tagtatttt      1650
cttccagctt tggtttttt ttatttgaac tatattttgg ttaattcctc      1700
ttgatattaa cctttatagt ttttcaggaa attagttaaa atccgttgta      1750
ttttatggtc cccatttagc gtccttcatg ggtggaagtt tttatgtgac      1800
acaaggctga taaaaggtt aaattttta gttattttct caccaggctg      1850
gggttttttc ttcagtcttg aacaaacaac tgaaatttgg cttaagtaag      1900
tcctccttga tattaaccat ttattagtct taattataaa accctatact      1950
ttgtaggtta tcattttttc tccttttttg ctaaatttat gggcaatccc      2000
ttccaagtat ttgtcaaatt tagtgtgaag aaacttaaaa gcaaggtacc      2050
aaaagtgtca tagtattaaa acttctattt accttattta ttttaaaaaa      2100
attgttatat tcacttgatt tctcccttg catgtttggt tttgagtatg      2150
aagacttaat ggctataaca aatatctcag aaaactcctt taacaaaaat      2200
ccttcctaat taaatgaagg aatgatgtgt tatctgtttt cattcattca      2250
acaaatattt gggtacatta gtgctatgta ttattgggtg ctgggtagct      2300
tggtatatat cagtttaaaa agacagaaat tcctgcccct tgtggagtgag      2350
aaaaacagac aataaacata taaggcata aagattctga ataggcagtt      2400
gattatagaa attgaaattc aagggaggag tctgaattgc agatatgaat      2450
tagggtacca tcaatgtgta gggaaccatg gggtcaggat aaaatcaata      2500
aagaagtaat tgagatagag aaaagagaaa agtctgagga ccaagcctga      2550
ggcactccag aatttagaga ttaggtggat gagaagtaac tagcagaaaa      2600
gactagaaaa ggaggggcca gtgagatagg aaaattagga caatgaagtg      2650
ttttgaggaa aagagtatat aaagtacctt ttcaaatgtt gcacatagat      2700
```

-continued

| | |
|---|---|
| taaggatcat atatattaag acctgaccat tggattttag agaagtgagg | 2750 |
| ggagaggata aaaagtctg actgtaattt aaaagaaata agaagaggag | 2800 |
| caattggaga cagactagaa aactctaaaa atgttttcct tataaagggg | 2850 |
| aacagagaaa aggggtagta gctgaaagag gattgggggc atagtcaaga | 2900 |
| gaaattatca catgtaatta gtaaatgata taatagaatt tgaggccagg | 2950 |
| cgcggtggct cacacctgta atcccagcac tttgggaggc cgaggcggca | 3000 |
| gatcacaagg tcaagagatt gagaccatcc tggccaacat ggtgaaaccc | 3050 |
| cgtctctact aaaaatacaa aaattagctg ggcgtggtgg tgcgtgcctg | 3100 |
| tagtcccagc tactcgggag gctgaggcag gagaatcctt gaacaggagg | 3150 |
| cggaggttgc agtgagccga gattgtgcca tgcactccag cctacctgta | 3200 |
| gtcccagcta ctcgggaggc tgaggcagga gaatcacttg aacccaggag | 3250 |
| gtggaggttg cagtgagccg agattgcgcc actgcactcc agcctacctg | 3300 |
| tagtcccagc tacttgggag atgaggcagg agaatcgctt gaacccggga | 3350 |
| ggcagaggtt gcagtgagcc aagattgcac cactacactc cagcctgggg | 3400 |
| acagaatgag actccgtcaa aaaaaaaaaa aaaaactcga gagtacttct | 3450 |
| agagcggccg cgggcccatc gattttccac ccgggtgggg taccaggtaa | 3500 |
| gtgtacccgt cg | 3512 |

<210> SEQ ID NO 10
<211> LENGTH: 2634
<212> TYPE: DNA
<213> ORGANISM: Unknown
<220> FEATURE:
<221> NAME/KEY: prim_transcript
<223> OTHER INFORMATION: complete sequence of clone 5.28 encoding a melanoma tumor-associated antigen

<400> SEQUENCE: 10

| | |
|---|---|
| ggacgccgct ggagctccgc gcctgcaggt cgacactagt ggatccaaag | 50 |
| aattcggcac cagcctgcag gtactgctgc tcgtgcctcc ggctccggcc | 100 |
| cctgagcgat ggtcctttcc ttctgccacg gcgggatcgg gcactcaccc | 150 |
| agttgcaagt gcgagcacta tggagtagcg cagggtctcg agctgtggcc | 200 |
| gtggacttag gcaacaggaa attagaaata tcttctggaa agctggccag | 250 |
| atttgcagat ggctctgctg tagtacagtc aggtgacact gcagtaatgg | 300 |
| tcacagcggt cataaaacaa aaccttcccc ttcccagttt atgcctttgg | 350 |
| tggttgacta cagacaaaaa gctgctgcag caggtagaat tcccacaaac | 400 |
| tatctgagaa gagaggttgg tacttctgat aaagaaattc taacaagtcg | 450 |
| aataatagat cgttcaatta ggaccgctct ttccagctgg ctacttctat | 500 |
| gatacacagg ttctgtgtaa tctgttagca gtagatggtg taaatgagcc | 550 |
| tgatgtccta gcaattaatg cgcttcgta gccctctcat tatcagatat | 600 |
| tccttggaat ggacctgttg gggcagtacg aataggaata attgatggag | 650 |
| aatatgttgt taacccaaca agaaaagaaa tgtcttctag tactttaaat | 700 |
| ttagtggttg ctggagcacc taaaagtcag attgtcatgt ggaagcctc | 750 |
| tgcagagaac attttacagc aggacttttg ccatgctatc aaagtgggag | 800 |
| tgaaatatac ccaacaaata attcagggca ttcagcagtt ggtaaaagaa | 850 |

```
actggtgtta ccaagaggac acctcagaag ttatttaccc cttcgccaga        900
gattgtgaaa tatactcata aacttgctat ggagagactc tatgcagttt        950
ttacagatta cgagcatgac aaagtttcca gagatgaagc tgttaacaaa       1000
ataagattag atacggagga acaactaaaa gaaaaatttc agaagcccg        1050
atccatatga aataatagaa tccttcaatg ttgttgcaaa ggaagttttt       1100
agaagtattg ttttgaatga atacaaaagg tgcgatggtc gggatttgac       1150
ttcacttagg aatgtaagtt gtgaggtaga tatgtttaaa acccttcatg       1200
gatcagcatt atttcaaaga ggacaaacac aggtgctttg taccgttaca       1250
tttgattcat tagaatctgg tattaagtca gatcaagtta taacagctat       1300
aaatgggata aagataaaa atttcatgct gcactacgag tttcctcctt        1350
atgcaactaa tgaaattggc aaagtcactg gtttaaatag aagagaactt       1400
gggcatggtg ctcttgctga gaaagctttg tatcctgtta ttcccagaga       1450
ttttcctttc accataagag ttacatctga agtcctagag tcaaatgggt       1500
catcttctat ggcatctgca tgtggcggaa gtttagcatt aatggattca       1550
ggggttccaa tttcatctgc tgttgcaggc gtagcaatag gattggtcac       1600
caaaaccgat cctgagaagg gtgaaataga agattatcgt ttgctgacag       1650
atattttggg aattgaagat tacaatgtga catggacttc aaaatagctg       1700
gcacttaata aaggaataac tgcattacag gctgatatta aattacctgg       1750
aataccaata aaaattgtga tggaggctat tcaacaagct tcagtggcaa       1800
aaaaggagat attacagatc atgaacaaaa ctatttcaaa acctcgagca       1850
tctagaaaag aaaatggacc tgttgtagaa actgttcagg ttccattatc       1900
aaaacgagca aaatttgttg gacctggtgg ctataactta aaaaaacttc       1950
aggctgaaac aggtgtaact attagtcagg tggatgaaga aacgttttct       2000
gtatttgcac caacacccag tgctatgcat gaggcaagag acttcattac       2050
tgaaatctgc aaggatgatc aggagcagca attagaattt ggagcagtat       2100
ataccgccac aataactgaa atcagagata ctggtgtaat ggtaaaatta       2150
tatccaaata tggctgcggt actgcttcat aacacacaac ttgatcaacg       2200
aaagattaaa catcctactg ccctaggatt agaagttggc caagaaattc       2250
aggtgaaata ctttggacgt gacccagccg atggaagaat gaggctttct       2300
cgaaaagtgc ttcagtcgcc agctacaacc gtggtcagaa ctttgaatgc       2350
agaagtagta ttgtaatggg agaacctatt ccagtcatcc atctaattct       2400
cagtgatttt ttttttttaa agagaattct agaattctat tttgtctagg       2450
gtgatgtgct gtagagcaac attttagtag tatcttccat tgtgtagatt       2500
tctatataat ataaatacat tttaattatt tgtactaaaa aaaaaaaaaa       2550
aaaactcgag agtacttcta gagcgggccg cgggcccatc gattttccac       2600
ccgggggggt accaggtaag tgtcccggct cacc                        2634
```

<210> SEQ ID NO 11
<211> LENGTH: 673
<212> TYPE: DNA
<213> ORGANISM: Unknown
<220> FEATURE:

<221> NAME/KEY: mat_peptide
<222> LOCATION: 3,4,5,6,16,21,580,590,654,668
<223> OTHER INFORMATION: 5' end of clone 5.31 encoding a melanoma
      tumor-associated antigen; n = unknown

<400> SEQUENCE: 11

| | | | | |
|---|---|---|---|---|
| ggnnnntttg | tttatnacac | nccagctcga | aattaaccct | cactaaaggg | 50 |
| aacaaaagct | ggagctcgcg | cgcctgcagg | tcgacactag | tggatccaaa | 100 |
| gaattcggca | cgaggtgtta | ccagtgccca | tcaggtgcct | gccgtctctt | 150 |
| ctgtgtcaca | cacagccctg | tatactcctc | cacctgagat | acctaccact | 200 |
| gtcctcaaca | ttccccaccc | atcagtcatt | tcctctccac | ttctcaagtc | 250 |
| cttgcactct | gctgaccccc | cgctccttgc | tgttactgca | gctcctccag | 300 |
| cccagcccct | tgccaaggta | tgatctgtgg | atttcctctg | gcagcaggg  | 350 |
| aggcaagggt | cttaagtaaa | gtgggcttgg | agtgacaggt | tccctatctt | 400 |
| gtttctttct | gcagaaaaaa | ggcgtaaagc | ggaaagcaga | tactaccacc | 450 |
| cctacaccta | cagccatctt | ggctcctggt | tctccagcta | gccctcctgg | 500 |
| gagtcttgag | cctaaggcag | cacggcttcc | cctatgcgta | gagagagtgg | 550 |
| tcgcccatca | agcccccacg | caaagacttn | ctgactctan | caacaacacc | 600 |
| agactctaag | aaaggaaagc | tttagaacag | ttaaacattg | caatggattt | 650 |
| tgangagtac | tctctaanaa | cat | | | 673 |

<210> SEQ ID NO 12
<211> LENGTH: 593
<212> TYPE: DNA
<213> ORGANISM: Unknown
<220> FEATURE:
<223> OTHER INFORMATION: 3' end of clone 5.31 encoding a melanoma
      tumor-associated antigen

<400> SEQUENCE: 12

| | | | | |
|---|---|---|---|---|
| ttgaaaataa | tgatgggagt | ttttttgtcat | gtgtgtgcaa | ctcaacgagg | 50 |
| tctcctgtct | gacagtgtaa | attggagcta | tatcacttgg | gggctgggag | 100 |
| tagggcctgt | ttatcagcat | agtttttgagt | ttggcctctt | tctaggatga | 150 |
| tttgagttcc | gttatgccaa | gatgccagat | gaaccactag | aaccagggcc | 200 |
| tttaccagtc | tctactgcca | tgcccctgg  | cttggccaaa | tcgtcttcag | 250 |
| agtcctccag | tgaggaaagt | agcagtgaga | gctcctctga | ggaagaggag | 300 |
| gaggaagatg | aggaggacga | ggaggaagaa | gagagtgaac | ctcagactca | 350 |
| gaggaagaaa | gggctcatcg | cttagcagaa | ctacaggaac | aggtattttg | 400 |
| tcactcttga | aagtttttat | tgggtaagag | gttcatgccc | tttgtcctca | 450 |
| ttttttcttc | ttgttatttt | atctttattt | acttttttcca | cttcatgttt | 500 |
| tttttccttt | agcttcgggc | agtacatgaa | caactggctg | ctctgtccca | 550 |
| gggtccaata | tccaagccca | agaggaaaaa | aaaaaaaaaa | aaa        | 593 |